(12) United States Patent
Kurakami et al.

(10) Patent No.: US 8,088,947 B2
(45) Date of Patent: Jan. 3, 2012

(54) METHOD FOR PRODUCING METHACROLEIN AND/OR METHACRYLIC ACID

(75) Inventors: Tatsuhiko Kurakami, Sanyoonoda (JP); Toshitake Kojima, Takasaki (JP); Yoshimasa Seo, Takasaki (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 512 days.

(21) Appl. No.: 12/223,494

(22) PCT Filed: Mar. 30, 2007

(86) PCT No.: PCT/JP2007/057069
§ 371 (c)(1),
(2), (4) Date: Jul. 31, 2008

(87) PCT Pub. No.: WO2007/119607
PCT Pub. Date: Oct. 25, 2007

(65) Prior Publication Data
US 2009/0062564 A1 Mar. 5, 2009

(30) Foreign Application Priority Data
Apr. 3, 2006 (JP) ................................. 2006-101459

(51) Int. Cl.
*C07C 51/12* (2006.01)
*C07C 51/14* (2006.01)
*C07C 51/16* (2006.01)
*C07C 45/00* (2006.01)

(52) U.S. Cl. ......... 562/534; 562/519; 562/522; 568/475
(58) Field of Classification Search ................... 562/518, 562/521, 535, 519, 522, 534; 568/476, 475
See application file for complete search history.

(56) References Cited

U.S. PATENT DOCUMENTS

| 4,873,391 A | 10/1989 | Inoue et al. ................... 585/639 |
| 2005/0090695 A1 | 4/2005 | Nakamura et al. ............ 568/476 |

FOREIGN PATENT DOCUMENTS

| JP | 51-12605 | 4/1976 |
| JP | 63-41431 | 2/1988 |
| JP | 08-047642 | 2/1996 |
| JP | 2004-130261 | 4/2004 |
| JP | 2005-320315 | 11/2005 |
| JP | 63-216835 A | 2/2011 |

*Primary Examiner* — Taylor Victor Oh
(74) *Attorney, Agent, or Firm* — Nields, Lemack & Frame, LLC

(57) ABSTRACT

The present invention relates to a method for producing methacrolein and/or methacrylic acid characterized in that the catalyst filling length of a dehydration catalyst layer is 3 to 20% of the catalyst filling length of an oxidation catalyst layer in a method where raw material gas containing gaseous t-butanol is supplied to a fixed-bed multitubular reactor having a dehydration catalyst layer and an oxidation catalyst layer in this order, from the entrance for raw material gas toward the exit, to produce methacrolein and/or methacrylic acid by dehydration reaction and catalytic gas phase oxidation reaction, and the present invention can increase the conventional yield of approximately 80% to 81 to 82% even when a reaction bath temperature is relatively low (approximately 355° C.).

5 Claims, No Drawings

METHOD FOR PRODUCING METHACROLEIN AND/OR METHACRYLIC ACID

TECHNICAL FIELD

The present invention relates to a method for producing methacrolein and/or methacrylic acid.

BACKGROUND OF THE INVENTION

As a method for producing methacrolein and/or methacrylic acid using isobutylene or tertiary butylalcohol (hereinafter, referred to as tertiary butanol) as a raw material by fixed-bed catalytic gas phase oxidation reaction is already well known, various complex oxide catalysts for it have been proposed. Among them, a method using tertiary butanol (hereinafter, also referred to as t-butanol), which is in a liquid state at ordinary- temperatures, as a raw material costs lower than using isobutylene which is in a gas state at ordinary temperatures, and is frequently used as a raw material. A production process of methacrolein and/or methacrylic acid using t-butanol as a raw material will be illustrated as follows.

(1) First of all, t-butanol is heated to no lower than its boiling point for vaporization, which is then mixed with a gas containing at least oxygen to obtain a raw material mixed gas, otherwise t-butanol in a liquid state is, for example, atomized and then mixed with a gas containing at least oxygen, and then said mixture is heated to no lower than the boiling point of t-butanol for vaporization of the t-butanol to obtain a raw material mixed gas.

(2) Subsequently, the resulting mixed gas (a raw material gas) is passed through a dehydration catalyst to decompose part of t-butanol into isobutylene and water by dehydration reaction and then supplied; otherwise the resulting mixed gas is not sent through said dehydration catalyst and directly supplied; to an oxidation catalyst layer maintained at a predetermined temperature to obtain methacrolein and/or methacrylic acid by catalytic gas phase oxidation reaction.

As described above, t-butanol vaporized is, in many cases, used in the same way as isobutylene is used.

There are a lot of reports that the yield of methacrolein and methacrylic acid by using t-butanol as a raw material is usually the same as by using isobutylene as a raw material.

On the other hand, it is known that a dehydration reaction of t-butanol with a dehydration catalyst is an endothermic reaction, and because said endothermic reaction has adverse effects on the following oxidation reaction, several methods to avoid it have been proposed. For example, in Patent Literature 1, there is described a method to obtain methacrolein and /or methacrylic acid in a good yield, where no lower than 50% of t-butanol is decomposed into isobutylene and water by dehydration reaction with oxidation catalyst in advance and supplied to an oxidation catalyst layer. In said Patent Literature, it is specifically described that gamma-alumina-silica (γ-alumina: 90%, silica: 10%) of dehydration catalyst is charged into a gas mixer and inert α-alumina-silica is charged as a preheating layer in a reaction tube, at a length of 80 cm (whole length of the reaction tube: 2 m), to dehydrate t-butanol to isobutylene, and then the isobutylene is then turned to methacrolein and methacrylic acid by oxidation reaction.

Also in Examples 16 and 17 of Patent Literature 2, there is described an example where 20 ml of silicon carbide or α-alumina based on 3 ml of a catalyst is charged for dehydration of t-butanol to turn it to methacrolein and methacrylic acid by catalytic gas phase oxidation reaction.

Patent Literature 1: JP 63-216835 A
Patent Literature 2: JP 51-12605 B

DISCLOSURE OF THE INVENTION

Problems to Be Solved by the Invention

The method for producing methacrolein and methacrylic acid from t-butanol is established industrially and the yield and the like are relatively close to the limits, however, even small improvement of yield, decrease of reaction temperature and the like can make big difference industrially because of the high production volume of methacrolein and methacrylic acid. Therefore, further improvement of yield, decrease of reaction temperature and the like are required. In the above method of Patent Literature 1, there may be caused somewhat of a problem in terms of the catalyst life because the reaction bath temperature is high although the yield is relatively good, and in the above method of Patent Literature 2, there is a problem in terms of industrial implementation because the reaction temperature is low at 350 to 360° C. but the yield is also low. Therefore, development of a method to provide a high yield even when the reaction bath temperature is low is required.

Means of Solving the Problems

The inventors of the present invention intensively studied under the situation and have found that in the method for producing methacrolein and/or methacrylic acid from t-butanol using a fixed-bed multitubular reactor, a specified ratio of the filling length of an oxidation catalyst layer and the filling length of catalyst in a dehydration catalyst layer can improve the yield even when the reaction temperature is low, and completed the present invention.

That is, the present invention relates to:

(1) A method for producing methacrolein and/or methacrylic acid, wherein t-butanol, a raw material, is supplied to a fixed-bed multitubular reactor having a dehydration catalyst layer and an oxidation catalyst layer for dehydration to obtain water and isobutylene and the isobutylene is oxidized to produce methacrolein and/or methacrylic acid, and characterized in that the filling length of catalyst in the dehydration catalyst layer which is contacted by t-butanol before supplying the t-butanol to the oxidation catalyst layer is 3 to 20% of the filling length of catalyst in the oxidation catalyst layer, (2) The method according to the above (1), wherein a dehydration catalyst is alumina or alumina-silica, (3) The method according to the above (1) or the above (2), wherein a temperature of the dehydration catalyst layer is 250 to 400° C., (4) The method according to the above (1), wherein an oxidation catalyst is of a complex metal oxide comprising molybdenum, bismuth, ion and cobalt as constitutional elements, (5) The method according to the above (4), wherein the oxidation catalyst is a catalyst having a complex oxide represented by the following formula, $$Mo_a Bi_b Fe_c Co_p d X_e Y_f O_h$$

(wherein, Mo, Bi, Fe and Co represent molybdenum, bismuth, ion, and cobalt respectively. X represents one or more elements selected from an alkali metal or TI, and Y represents one or more elements selected from Ni, Sn, Zn, W, Cr, Ce, Mn, Mg, Sb or Ti. The additional characters on the bottom-right of the symbols of the elements are atomic ratios of the elements, b=0.1 to 10, c=0.1 to 10, d=1 to 10, e=0.01 to 2, and f=0 to 2 when a=13, and h is a numeric number determined according to an oxidation state of each element), as a catalyst active component.

Effect of the Invention

According to the present invention, the yield of methacrolein and/or methacrylic acid from t-butanol can be improved in an easy process even when the reaction bath temperature is low. Therefore, the production method of the present invention is extremely useful industrially.

BEST MODE FOR CARRYING OUT THE INVENTION

The present invention improves the yield of methacrolein and/or methacrylic acid by a specified length ratio of the filling layers of a dehydration catalyst filling layer and an oxidation catalyst filling layer, that is, the length of said dehydration catalyst filling layer (hereinafter, also referred to as dehydration catalyst filling length) is 3 to 20% of the length of the oxidation catalyst filling layer (also referred to as oxidation catalyst filling length), preferably 5 to 17%, further preferably 6 to 17%, in the production method of methacrolein and/or methacrylic acid from t-butanol by catalytic gas phase oxidation in a fixed-bed multitubular reactor. And optionally, the dehydration catalyst filling length is most preferably approximately 5 to 15% of the length of oxidation catalyst filling layer.

In the present invention, it is usually preferred that a dehydration catalyst is charged into a reaction tube filled with an oxidation catalyst, on the entrance side for raw material gas in front of the oxidation catalyst. Otherwise, the dehydration catalyst may be charged into another tube having the same inside diameter as the reaction tube filled with the oxidation catalyst, which tube is connected to the reaction tube filled with the oxidation catalyst so that reaction gas coming out of the tube can be supplied to the reaction tube.

In this connection, in the present invention, a filling length of catalyst means a length of catalyst filled into a reaction tube from the entrance toward the exit for reaction gas.

In a fixed-bed multitubular reactor to be used for production of methacrolein and/or methacrylic acid to be usually used, a reaction tube usually has an inside diameter of 15 to 50 mm, preferably approximately 15 to 40 mm, further preferably 18 to 30 mm, and a length of 1 m to 5 m, preferably approximately 2 m to 4 m, where an oxidation catalyst is filled. In the present invention, a dehydration catalyst is preferably charged into said reaction tube together with an oxidation catalyst, and in such a case, the dehydration catalyst layer is provided closer to the side of the entrance for raw material gas than the oxidation catalyst layer.

An optimum amount of dehydration catalyst to be used is preferably determined accordingly in the range of satisfying the above ratio of the present invention relative to the catalyst filling length to be used for oxidation reaction in accordance with conditions of the rate of feed of mixed gas containing t-butanol, the temperature of the dehydration catalyst layer, the type of catalyst, the diameter of catalyst and the like.

It is usually easy and preferable in terms of operating manipulation that the bath temperature of the dehydration catalyst layer is the same as that of the oxidation catalyst layer, however optionally, the bath temperatures of the dehydration catalyst layer and the oxidation catalyst layer may be controlled differently. Even when the bath temperatures are usually the same, the temperature of the catalyst layer tends to decrease due to endothermic reaction in the dehydration catalyst layer and the bath temperature of the oxidation catalyst layer tends to increase because an oxidation reaction is an exothermic reaction.

When the method of the present invention is carried out industrially, it is usually preferred that operation is performed in order that the residual isobutylene in the gas at the exit of the above reactor is maintained constant. Therefore, the reaction is preferably carried out at a lower temperature of the oxidation catalyst layer at the early stage of the reaction when the catalyst activity is usually high and at an increased temperature of the oxidation catalyst layer at the later stage of the reaction when the catalyst comes to deteriorate due to long use. In this case, because the reaction bath temperature is increased along with deterioration of the catalyst, the temperature of the dehydration catalyst layer is also influenced by the increase of the reaction bath temperature when both the temperatures of the dehydration catalyst layer and the oxidation catalyst layer are controlled in the same reaction bath.

In the present invention, the temperature of the dehydration catalyst layer is preferably 250 to 400° C., more preferably 300 to 370° C., further preferably approximately 330 to 370° C.

The shape of a dehydration catalyst is not particularly limited, and shapes such as columnar shape, spherical shape, Raschig ring shape and the like can be used. The size is not particularly limited but preferably a similar size as an oxidation catalyst, and a diameter of 3 to 10 mm is preferable when taking a spherical catalyst for example.

The dehydration catalyst to be used in the present invention is not particularly limited as long as it is capable of converting t-butanol to isobutylene by dehydration reaction. For example, solid acids such as boric acid and solid phosphoric acid; a silicon compound such as silicon carbide; a metal oxide such as alumina and alumina-silica; an alumina silicate compound such as natural or synthetic zeolite; and the like are included. Among them, alumina or a metal oxide containing alumina is preferable, and above all, a metal oxide containing α-alumina is more preferable. A metal oxide containing α-alumina is generally known as a compound with low dehydration activity of t-butanol, however, according to the study by the inventors of the present invention, a metal oxide containing α-alumina is easier and more preferable to use in the present invention than a compound with high dehydration activity, for example, such as γ-alumina. A compound with high dehydration activity such as γ-alumina can be also used in the present invention, but the production amount of by-product decomposed from t-butanol tends to be higher.

For a metal compound containing α-alumina, it is preferred to use alumina-silica, a mixture with silica, preferably composed of approximately 60 to 98 mol % of a-alumina, more preferably 70 to 95 mol %, further preferably 70 to 90 mol % and approximately 2 to 40 mol % of silica, more preferably approximately 5 to 30 mol %, further preferably 10 to 30 mol %. The contents of alumina and silica can be determined with a commercially available analytical instrument. For example, fluorescent X-ray analysis, X-ray photoelectron spectroscopy analysis and the like are included. In addition, said α-alumina-silica preferably has a specific surface area of approximately 0.02 to 1 m$^2$/g, more preferably, approximately 0.05 to 0.5 m$^2$/g.

The rate of feed (space velocity; an amount of gas feed (volume) per hour unit divided by the volume of a catalyst layer) of t-butanol to the dehydration layer may be typically 1000 to 100000 h$^{-1}$, preferably approximately 3000 to 50000 h$^{-1}$, and optionally 5000 to 100000 h$^1$.

In the present invention, a raw material gas containing t-butanol and molecular oxygen (for example, raw material gas composed of 1 to 10 mol % of t-butanol, 2 to 40 mol % of molecular oxygen, and inert gas for the rest) are passed into the dehydration catalyst layer and then the oxidation catalyst layer, in this sequence, of the reaction tube filled with a dehydration catalyst and an oxidation catalyst at the above length ratio of the filling layers, to subject to dehydration reaction and oxidation reaction and to produce methacrolein and/or methacrylic acid. In this connection, the above inert gas includes also gaseous water and the like which is inactive in the present reaction, other than nitrogen, argon and the like. In addition, a reaction tube to feed the above raw material gas may be separated into two reaction tubes for a dehydration catalyst layer and an oxidation catalyst layer, however, a reaction tube filled with the both catalysts in a fixed-bed multitubular reactor is usually preferable.

The above production method will be explained more specifically. Tertiary-butanol (usually containing approximately 10 and more weight % of water) as a raw material and usually air as molecular oxygen and inert gas, and if required, additional inert gas such as nitrogen or argon, are passed through a mixing bath to obtain a raw material mixed gas. The raw material mixed gas preferably contains air, and if required, additional inert gas, usually at a ratio of 10 to 40 mols of air and approximately 0 to 40 mols of additional inert gas based on 1 mol of t-butanol. The mixed bath is typically charged with inert Raschig rings or the like which do not participate in dehydration and oxidation reactions.

Subsequently, the resulting raw material mixed gas is introduced into an oxidation reactor at a space velocity (per unit volume of an oxidation catalyst) in the range of typically 700 to 3000 h$^{-1}$, preferably 1000 to 3000 h$^{-1}$. In the present invention, the oxidation reactor is typically filled with a dehydration catalyst of alumina, alumina-silica or the like and an oxidation catalyst in this sequence, from the entrance for raw material gas toward the exit, at the above ratio of the filling length of catalyst layers (the filling length of the dehydration catalyst layer is 3 to 20% of the filling length of the oxidation catalyst layer). The raw material gas introduced into the oxidation reactor is turned into objective methacrolein and/or methacrylic acid through dehydration reaction and oxidation reaction in the dehydration catalyst layer and the oxidation catalyst layer.

The oxidation reaction in the present invention is typically carried out at 320 to 400° C., preferably 340 to 380° C., more preferably approximately 340 to 360° C. The reaction temperature is maintained at a temperature close to the reaction bath temperature because a reaction tube in an oxidation reactor is usually in a reaction bath or is covered with a jacket to control a reaction temperature. Actual reaction temperature of the dehydration catalyst layer is lower than said bath temperature because a dehydration reaction is an endothermic reaction and practical reaction temperature of the oxidation catalyst layer is slightly higher than said bath temperature.

In this connection, catalytic oxidation reaction can be carried out under added pressure or under reduced pressure, however, usually suitably under a pressure in the vicinity of atmospheric pressure.

In addition, the raw material gas to be fed into the oxidation reactor in the present invention preferably contains t-butanol, molecular oxygen, and inert gas for the rest and substantially no isobutylene, and optionally the above raw material gas may be passed through a dehydration reactor provided separately from the oxidation reactor to decompose part of t-butanol into isobutylene and water, and then fed into the oxidation reactor. In such a case, a dehydration catalyst to be usually used may be used in a dehydration reactor provided separately.

Any oxidation catalyst can be used in the present invention as long as it can be used to obtain methacrolein (and methacrylic acid) by catalytic gas phase oxidation of t-butanol or isobutylene.

Typically, a catalyst called complex oxidation catalyst is used, preferably a complex metal oxide containing molybdenum, bismuth, iron and cobalt as component elements More preferable catalyst includes catalysts comprising a complex oxide represented by the following general formula,

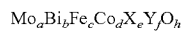

$$Mo_aBi_bFe_cCo_dX_eY_fO_h$$

(wherein, Mo, Bi, Fe and Co represent molybdenum, bismuth and cobalt respectively. X represents one or more elements selected from alkali metal or TI, and Y represents one or more elements selected from Ni, Sn, Zn, W, Cr, Ce, Mn, Mg, Sb or Ti. In addition, the additional characters on the bottom-right of the symbols of the elements are atomic ratios of the elements, b=0.1 to 10, c=0.1 to 10, d=1 to 10, e=0.01 to 2, and f=0 to 2 when a=13, and h is a numeric number determined according to an oxidation state of each element), as a catalyst active component.

The alkali metal is preferably Cs and X is also especially preferably Cs. Y preferably contains one or two of the above metals or no metal at all. Y is especially preferably Ni when comprised.

The preparation method and raw materials for the oxidation catalyst to be used in the present invention are not particularly limited, and any method and raw materials to be generally used to prepare this type of catalyst can be used for the preparation.

The shape of the oxidation catalyst is not particularly limited. For example, shapes such as columnar shape, tablet, spherical shape and ring shape can be selected in view of operating conditions (the space velocity of raw material gas, the temperature of oxidation reactor, and the diameter and the length of oxidation reactor). Typically preferable is a supported catalyst having a grain size of 3 to 6 mm, more preferably 3 to 5 mm, which supports a catalyst active component on a spherical carrier, especially an inert carrier such as silica or alumina. Said catalyst can be obtained in a conventional manner where precalcined powder containing elements corresponding to the catalyst composition is supported on an inert carrier having a grain size of 2 to 5 mm, more preferably 3 to 4 mm, to obtain a shaped catalyst, which catalyst is then calcined in a conventional manner. In this connection, precalcined powder can be obtained by precalcination, at a temperature of 350 to 550° C., of powder obtained by spray-drying of an aqueous solution or a suspension of a compound containing elements corresponding to the catalyst composition. And the supported amount of precalcined powder in an oxidation catalyst is approximately 25 to 70 weight % based on a shaped catalyst, more preferably 30 to 50 weight %. The precalcination temperature for the shaped catalyst is usually approximately 400 to 700° C., preferably approximately 450 to 600° C., further preferably 500 to 550° C.

The oxidation catalyst can be filled in a single layer, but in order to prevent the highest peak temperature of the oxidation catalyst layer from increasing, catalysts with different kinds of activity can be filled in multiple layers from the entrance for raw material toward the exit in such combinations as to increase the activity.

EXAMPLES

Hereinafter, the present invention will be explained specifically by Examples. In Examples, the conversion and the yield are calculated according to the following formulas.

T-butanol conversion (%)=(number of mols of reacted t-butanol)/(number of mols of supplied t-butanol)×100

Methacrolein yield (%)=(number of mols of produced methacrolein)/(number of mols of supplied t-butanol)×100

Methacrylic acid yield (%)=(number of mols of produced methacrylic acid)/(number of mols of supplied t-butanol)×100

Isobutylene yield (%)=(number of mols of isobutylene contained in product after reaction)/(number of mols of supplied t-butanol)×100

Example 1

(Preparation of catalyst)

While heating and stirring 2000 ml of distilled water, 450 g of ammonium molybdate and 15.3 g of cesium nitrate were dissolved therein to obtain an aqueous solution (A). Separately, 456 g of cobalt nitrate and 238 g of ferric nitrate were dissolved in 500 ml of distilled water to prepare an aqueous solution (B), and 190 g of bismuth nitrate was dissolved in 200 ml of distilled water turned acidic by addition of 48 ml of concentrated nitric acid to prepare an aqueous solution (C), respectively. The above aqueous solutions (B) and (C) are mixed with the above solution (A) in this sequence while strongly stirring, and the formed suspension was dried using a spray dryer to obtain dry powder, which dry powder was then calcined at 460° C. for 5 hours to obtain precalcined powder (D). At this time, the relative proportions of the catalyst active components except oxygen were Mo=13, Bi=2.0, Fe=3.0, Co=8.0, and Cs=0.4 in atomic ratio.

Then, precalcined powder (D) was supported on an inert carrier (alumina, grain size: 4.0 mm) at a ratio of 35 weight% based on a catalyst after shaping. The shaped product thus obtained was calcined at 520° C. for 5 hours to obtain an oxidation catalyst (grain size: 4.3 mm).

(Test of Oxidation Reaction)

Spherical alumina-silica granules as dehydration catalyst (α-alumina: 80 mol %—silica: 20 mol %, diameter: 5 mm, specific surface area: 0.1 m²) were filled as a upper layer of 20 cm length and the above supported oxidation catalyst was filled as the lower layer of 265 cm length in a stainless-steel reactor having an average inside diameter of 21.4 mm (whole length: 4 m) and equipping with a jacket to circulate molten salt as a heating medium and a thermocouple to measure the temperature of the catalyst layer were set on the tube axial, and the temperature of the reaction bath was maintained at 355° C. Through a mixing bath, 202 g/hr of t-butanol (containing 13 weight% of water), 507 L/hr of air, and 234 L/hr of nitrogen were passed, and the resulting raw material mixed gas was introduced into the oxidation reactor at a space velocity of 1000 h$^{-1}$ (per oxidation catalyst) and reaction was carried out. The reaction temperatures of the dehydration catalyst layer and the oxidation catalyst layer were 355° C. As a result of the reaction, the conversion of t-butanol was 100%, the yield of methacrolein was 79.5%, the yield of methacrylic acid was 2.7%, and the yield of isobutylene was 1.2%.

Example 2

In the same manner as in Example 1 except that the length of the dehydration catalyst layer was changed to 40 cm, reaction was carried out. As a result, the conversion of t-butanol was 100%, the yield of methacrolein was 79.7%, the yield of methacrylic acid was 2.8%, and the yield of isobutylene was 1.1%.

Comparative Example 1

In the same manner as in Example 1 except that the length of the dehydration catalyst layer was changed to 70 cm, reaction was carried out. As a result, the conversion of t-butanol was 100%, the yield of methacrolein was 78.4%, the yield of methacrylic acid was 2.3%, and the yield of isobutylene was 1.1%.

Comparative Example 2

In the same manner as in Example 1 except that the dehydration catalyst layer was lost, a raw material gas was directly introduced into the oxidation catalyst layer to carry out the reaction. As a result, the conversion of t-butanol was 100%, the yield of methacrolein was 79.4%, the yield of methacrylic acid was 1.9%, and the yield of isobutylene was 1.6%.

Example 3

(Preparation of Catalyst)

While heating and stirring 2000 ml of distilled water, 450 g of ammonium molybdate and 3.8 g of cesium nitrate were dissolved therein to obtain an aqueous solution (A). Separately, 456 g of cobalt nitrate and 158 g of ferric nitrate were dissolved in 500 ml of distilled water to prepare an aqueous solution (B), and 190 g of bismuth nitrate was dissolved in 200 ml of distilled water turned acidic by addition of 48 ml of concentrated nitric acid to prepare an aqueous solution (C), respectively. The above aqueous solutions (B) and (C) were mixed with the above solution (A) in this sequence while strongly stirring, and the formed suspension was dried using a spray dryer and then calcined at 460° C. for 5 hours to obtain precalcined powder (D). At this time, the relative proportions of the catalyst active components except oxygen were Mo=13, Bi=2.0, Fe=2.0, Co=8.0, and Cs=0.1 in atomic ratio.

Then, precalcined powder (D) was supported on an inert carrier (alumina, grain size: 4.0 mm) at a ratio of 40 weight % based on a catalyst after shaping. The shaped object thus obtained was calcined at 520° C. for 5 hours to obtain a supported oxidation catalyst.

(Test of Oxidation Reaction)

Spherical alumina-silica granules as dehydration catalyst (α-alumina: 80 mol %—silica: 20 mol %, diameter: 5 mm, specific surface area: 0.1 m²/g) were filled as the upper layer of 20 cm length and the above supported oxidation catalyst was filled as the lower layer of 265 cm length in a stainless-steel reactor having an average inside diameter of 21.4 mm (whole length: 4 m) and equipping with a jacket to circulate molten salt as a heating medium and a thermocouple on the tube axis to measure the temperature of the catalyst layer, and the temperature of the reaction bath was maintained at 355° C.

Before introduction of a raw material gas composed of 202 g/hr of t-butanol (containing 13 weight % of water), 507 L/hr of air, and 234 L/hr of nitrogen into the reactor, 57% of the t-butanol was decomposed into isobutylene and water in a dehydration apparatus provided separately. The gas was introduced into the oxidation reactor at a space velocity of 1000 h$^{-1}$ and reaction was carried out, and as a result, the conversion of t-butanol was 100%, the yield of methacrolein was 79.0%, the yield of methacrylic acid was 2.6%, and the yield of isobutylene was 1.0%.

Comparative Example 3

In the same manner as in Example 3 except that the dehydration catalyst layer was changed to 70 cm length, reaction was carried out. As a result, the conversion of t-butanol was 100%, the yield of methacrolein was 78.1%, the yield of methacrylic acid was 2.2%, and the yield of isobutylene was 1.0%.

As described above, the effective yield decreases when the filling length of the dehydration catalyst layer is too long, and the residual isobutylene increases with no dehydration catalyst layer.

INDUSTRIAL APPLICABILITY

According to the method of the present invention, the total yield of methacrolein and methacrylic acid from t-butanol, which is approximately 80% by a conventional method, increases by 1 to 2% to totally approximately 81 to 82% at a relatively lower reaction temperature being a reaction bath temperature of 355° C., so that its usefulness in industrial production is extremely high.

The invention claimed is:

1. A method for producing methacrolein and/or methacrylic acid, wherein tertiary butanol, a raw material, is supplied to a fixed-bed multitubular reactor with a dehydration catalyst layer and an oxidation catalyst layer for dehydration to obtain water and isobutylene and the isobutylene is oxidized to produce methacrolein and/or methacrylic acid, and characterized in that the filling length of catalyst in the dehydration catalyst layer which is contacted by tertiary butanol before supplying the tertiary butanol to the oxidation catalyst layer is 3 to 20% of the filling length of catalyst in the oxidation catalyst layer.

2. The method according to claim 1, wherein a dehydration catalyst is alumina or alumina-silica.

3. The method according to claim 1 or claim 2, wherein a temperature of the dehydration catalyst layer is 250 to 400° C.

4. The method according to claim 1, wherein an oxidation catalyst is a complex metal oxide comprising molybdenum, bismuth, iron, and cobalt as compositional elements.

5. The method according to claim 4, wherein the oxidation catalyst is a catalyst having a complex oxide represented by the following formula, $$Mo_aBi_bFe_cCo_dX_eY_fO_h$$

(wherein, Mo, Bi, Fe and Co represent molybdenum, bismuth, ion, and cobalt, respectively. X represents one or more elements selected from an alkali metal or Tl, and Y represents one or more elements selected from Ni, Sn, Zn, W, Cr, Ce, Mn, Mg, Sb or Ti, the additional characters on the bottom-right of the symbols of the elements are atomic ratios of the elements, b=0.1 to 10, c=0.1 to 10, d=1 to 10, e=0.01 to 2, and f=0 to 2 when a=13, and h is a numeric number determined according to an oxidation state of each element), as a catalyst active component.

* * * * *